United States Patent [19]

Rosendal

[11] Patent Number: Plant 5,914

[45] Date of Patent: Mar. 24, 1987

[54] DOUBLE EXACUM WHITE

[75] Inventor: Erik Rosendal, Assens, Denmark

[73] Assignee: Nurserymen's Exchange, San Francisco, Calif.

[21] Appl. No.: 711,126

[22] Filed: Mar. 12, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of Exacum plant characterized by double flowers, floriferousness, blooming habits and the sterility of the flower. Plants can be propagated by asexual processes true to type. Rooting ability of the variety is excellent. The size of the flower surpasses that of the known single cultivar.

2 Drawing Figures

BACKGROUND OF THE NEW PLANT

The present new variety "White Rococo" was discovered by me in a commercial greenhouse in Denmark as a spontaneous mutant within a large number of the Exacum Affine Balf. cultivar "Pure white" grown as pot plants.

Asexual propagation of my new cultivar by cuttings in my greenhouse through several generations, proved that the new cultivar is true to type, and constant in its characteristics. Descriptions were carried out on Feb. 12, 1984. Color readings were based on The Royal Horticultural Society's Colour Chart.

DESCRIPTION OF DRAWINGS

The new plant is illustrated in the accompanying drawings in which.

BRIEF SUMMARY

Figure 1:
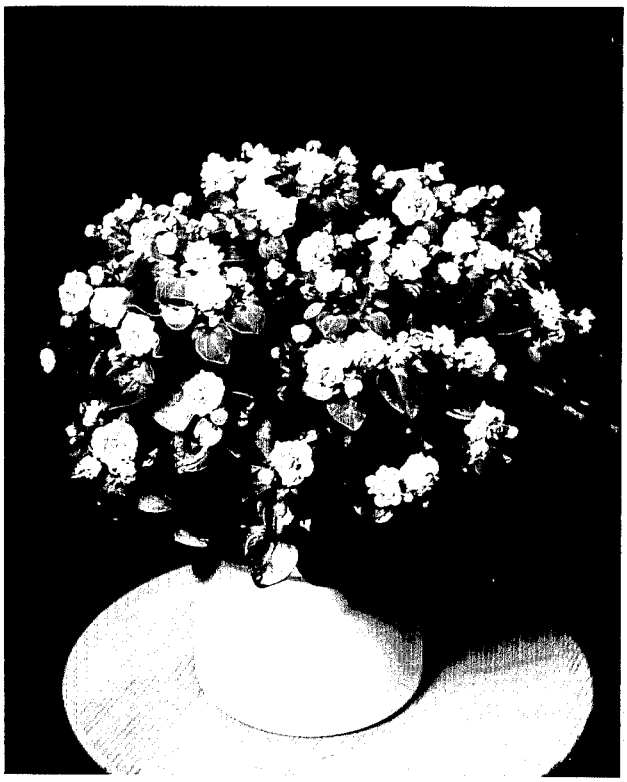
FIG. 1 is a full-color photograph of a potted plant in full bloom.
Figure 2:
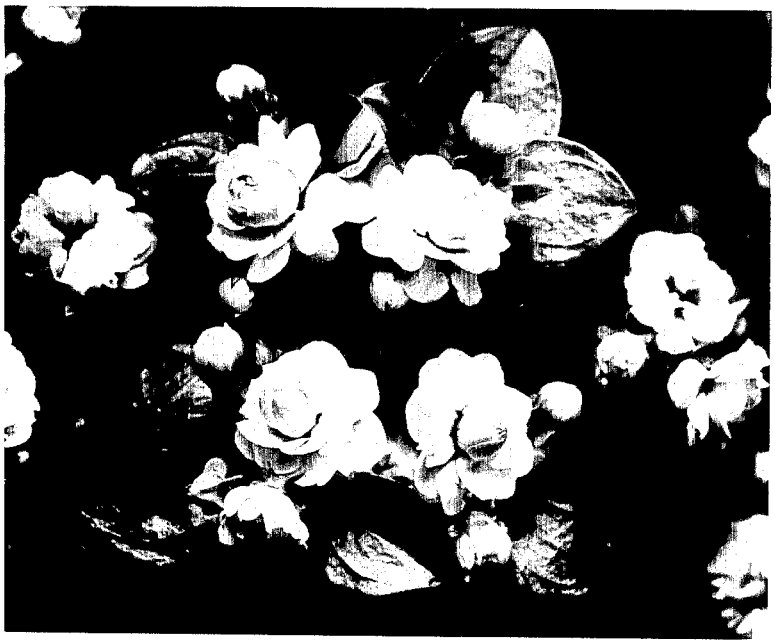
FIG. 2 is a full-color photograph of the blossoms of the plant.

Exacum "White Rococo" is a characteristic new mutant from a known seed propagated cultivar "PURE WHITE" and distinguishable from its origin:

1. The flowers are double.
2. Growth rate is equal to single-flowered seed-propagated cultivars.
3. Growth habit as potted plants is compact with an excellent branching ability.
4. The flowers are larger than in the single-flowered cultivars.
5. Stigma and stamens are present, but malformed as most of these have become petalloid or staminoid.
6. The flowers are sterile and produce no seed.
7. Reproduces easily with cuttings.
8. The keepability of the flower is better than for the single-flowered cultivars.

The accompanying color photograph illustrates the overall appearance of the cultivar "White Rococo." The flower color is white at full maturity, greenish white as bud. The following is based on observations made on Feb. 12, 1984.

PLANT

Origin: Mutation in a well defined seed-grown cultivar "Pure White."

Form: Upright with a distinct dichotomous branching ability right from base to the terminal shoots.
Height: To flowering 18–25 cm.
Plant diameter: Similar to height.
Growth rate: Fast under good light condition.
Type of cutting: Terminal shoots or stem segments.
Rooting time: 12–14 days.
Rooting habit: Fast and dense.

FOLIAGE

Arrangements: Opposite leaves at all nodes.
Shape of leaves: Broadly ovate.
Tip: Rounded.
Base: Obtuse to truncate.
Margin: Entire.
Venation: Three-veined from petiole. Middle vein strongest.
Size: Leaf-blade and petiole 40–60 mm. Length of blade 25–45 mm. Width at widest point 28–45 mm.
Surface: Smooth, with slightly depressed veins.
Texture: Glabrous.
Variegation: None.
Color:
*Petiole.*—144 A.
*Veins.*—144 B.
*Leaf surface.*—137 C, lower side — 143 C.

STEM

Color: 144 C — at internodes purplish tinted.
Length of internodes: 30–40 mm.
Structure: Strong, rounded quadrangular.
Breaking action: Sympodial. Flowers solitary in dichasia. Each node with two lateral shoots.

FLOWER

Form: Round.
Born: Solitary, terminal in dichasia.
Blossom: 18 to 25 mm in diameter.
Bud: Round, 8–11 mm in diameter. Color 145 C.
Calyx: 5 winged. Color 143 B.
Petals: The number varies from 12–18. Outer petals arranged as a collar around a 5–7 mm broad center of incurved petals changing in color from greenish to white. A fully open flower will normally consist of 12–14 spreading petals on an elongation of the floral parts.
Stamens: Short stamens are placed above and between petals and petalloid stamens.

Petal color: White with a greenish base, lower side 149 D at base.

Lasting quality: Average keepability one week depending on temperature.

Behaviour: The large number of flowers appear as an eye catcher at the surface of the compact green foliage. Wilted flowers bend down and do not spoil the general appearance as much as in single-flowered cultivars.

Pedicels: 15–25 mm purplish green.

Having thus disclosed my invention, I claim:

1. "White Rococo" to be a new and distinct cultivar of Exacum as shown and described, characterized by double white flowers, its floriferousness, its blooming habits, by the sterility of the flower, by its ability to be propagated by asexual processes true to type, having excellent rooting ability, and wherein the size of the flower is 18 to 25 mm in diameter, surpassing that of the known single cultivars.

* * * * *